(12) United States Patent
Xie

(10) Patent No.: US 6,783,504 B1
(45) Date of Patent: Aug. 31, 2004

(54) METHOD OF ACUPUNCTURE AND MAGNETIC TREATMENT FOR WEIGHT LOSS

(76) Inventor: Robert Be Xie, 2333 Mowry Ave., Fremont, CA (US) 94538

( * ) Notice: Subject to any disclaimer, the term of this patent is extended or adjusted under 35 U.S.C. 154(b) by 50 days.

(21) Appl. No.: 10/375,295

(22) Filed: Feb. 26, 2003

(51) Int. Cl.[7] .............................. A61N 1/00; A61B 17/34
(52) U.S. Cl. ........................................ 600/615; 606/189
(58) Field of Search ............... 600/9–15; 128/897–898; 606/189, 204

(56) References Cited

U.S. PATENT DOCUMENTS

| | | | |
|---|---|---|---|
| 4,033,054 A | | 7/1977 | Fukuoka |
| 4,798,194 A | * | 1/1989 | Amishima ...................... 600/9 |
| 5,803,896 A | * | 9/1998 | Chen ............................. 600/9 |
| 5,904,926 A | | 5/1999 | Slavin |
| 5,965,282 A | | 10/1999 | Baermann |
| 5,989,574 A | | 11/1999 | Slavin |
| 6,113,620 A | | 9/2000 | Chung |
| 6,159,145 A | | 12/2000 | Satoh |
| 6,285,905 B1 | * | 9/2001 | Chiang et al. .................. 607/2 |
| 6,421,560 B1 | * | 7/2002 | Yoo ............................ 600/548 |
| 2002/0169357 A1 | * | 11/2002 | Chen ............................ 600/15 |

* cited by examiner

*Primary Examiner*—Samuel G. Gilbert
(74) *Attorney, Agent, or Firm*—Intellectual Property Law Group LLP; Otto O. Lee; Juneko Jackson

(57) ABSTRACT

A method for effective weight loss without negative or harmful side effects as well as for the treatment of ailments in human patients. Treatment is achieved using a combination of acupuncture and magnets. The method includes the steps of placing several acupuncture needles into specified locations on the human body, removing the acupuncture needles, and placing several magnets onto the same locations that the needles previously occupied. Another important object of the present invention is to provide and effective method of coping with and managing diabetes.

47 Claims, 3 Drawing Sheets

METHOD OF ACUPUNCTURE AND MAGNETIC TREATMENT FOR WEIGHT LOSS

BACKGROUND OF THE INVENTION

In the United States, excess weight is a problem and the number of people becoming overweight continues to rise. A 1999 National Health and Nutrition Examination Survey concluded that 61% of American adults are overweight or obese. People who are overweight or obese are more prone to ailments such as high blood pressure, heart disease, and diabetes.

To combat excess weight and the associated conditions, many search for ways to lose weight. Annually, Americans spent over $33 billion on weight reduction products. Of the 50 million Americans who use a weight loss method, fewer than 5% will maintain their lower weight. With such a low success rate, people continue to search for ways to lose weight.

Acupuncture has long been used to treat anxiety, back pain, high blood pressure, and osteoarthritis. However, people are also turning towards acupuncture as a treatment for weight loss. Acupuncture is the ancient Chinese art of inserting fine needles under the surface of the skin into specific locations on the body to treat ailments.

Acupuncturists have charted points along numerous paths, called meridians, on the body. Many of the meridians are considered to affect various body organs and in turn are important in treating various ailments. Thin, solid needles are placed in one of several locations on the body called points. The number of needles and their location depends on the condition and its severity. Acupuncturists treat conditions by placing needles into the various points associated with that condition.

People also use magnets as a treatment for their health conditions, The increased demand for using magnets as a treatment option have led to an increase in the number of health products containing magnets. Products such as bracelets, insoles, pads, and clothing all contain magnets which people use to treat numerous ailments. Currently, these products use magnets more for the treatment of pain than excess weight or obesity.

Given the overweight and obese condition of many people, there remains a need for an effective method of helping people lose weight. Attempts at addressing the problem of excess weight are found in numerous U.S. Patents. Satoh (U.S. Pat. No. 6,159,145) discloses a tool with a magnetic stimulus for placement within the ear. The tool effectuates weight loss by providing a magnetic stimulus to the nerves and influences the sense of taste and appetite. However, the Satoh patent requires the constant presence of a foreign object in the wearer's ear, internal application of the magnets, and affects a user's sense of taste.

Chung (U.S. Pat. No. 6,113,620) describes an acupuncture needle with a magnet seated in the head. The needle seeks to achieve the same results of pain relief and disease treatment as commonly found in acupuncture. While dealing with magnets and acupuncture, this patent does not address the issue of weight loss or the specific placement of the needles to achieve weight loss.

Other prior art involves clothing containing magnets for the topical placement of magnets in strategic locations aimed at weight reduction. However, the shorts do not take into account the use of acupuncture treatment to further aid in weight reduction.

SUMMARY OF THE INVENTION

An important object of the present invention is to provide a method for treatment of ailments in human patients. Treatment is achieved using a combination of acupuncture and magnets.

The method comprises the steps of placing several acupuncture needles into specified locations on the human body, removing the acupuncture needles, and placing several magnets onto the same locations that the needles previously occupied.

Another important object of the present invention is to provide an effective means of weight loss without negative or harmful side effects.

Another important object of the present invention is to provide and effective means of coping with and managing diabetes.

These and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Figure 1:
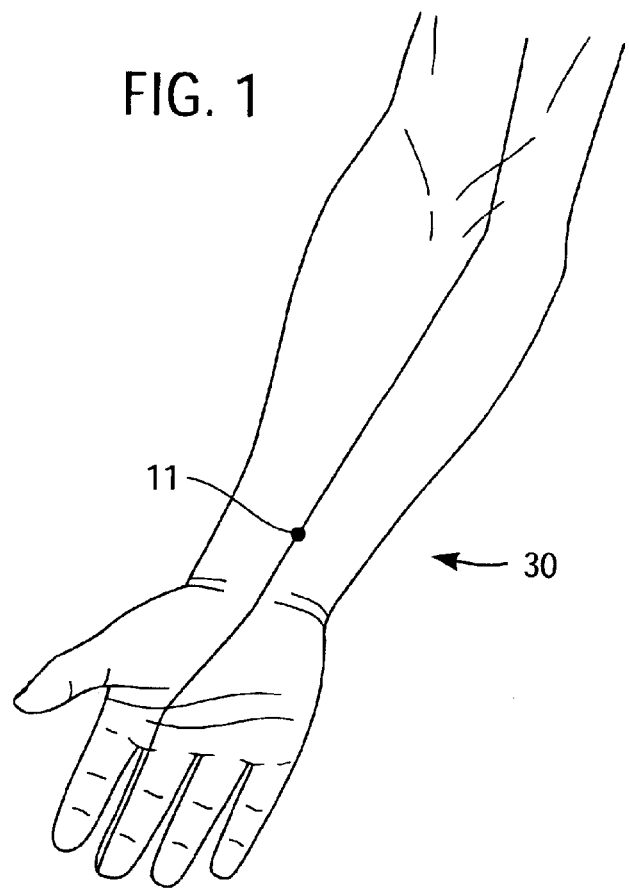
FIG. 1 illustrates a ventral side of a human left forearm and hand showing locations for needle and magnet placement in one embodiment of the invention.
Figure 3:
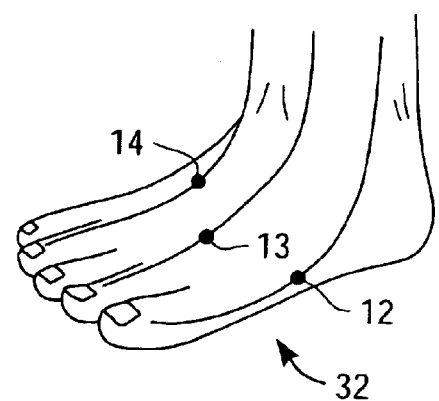
FIG. 3 is a perspective view of the dorsal side of a human right foot showing locations for needle and magnet placement in one embodiment of the invention.
Figure 4:
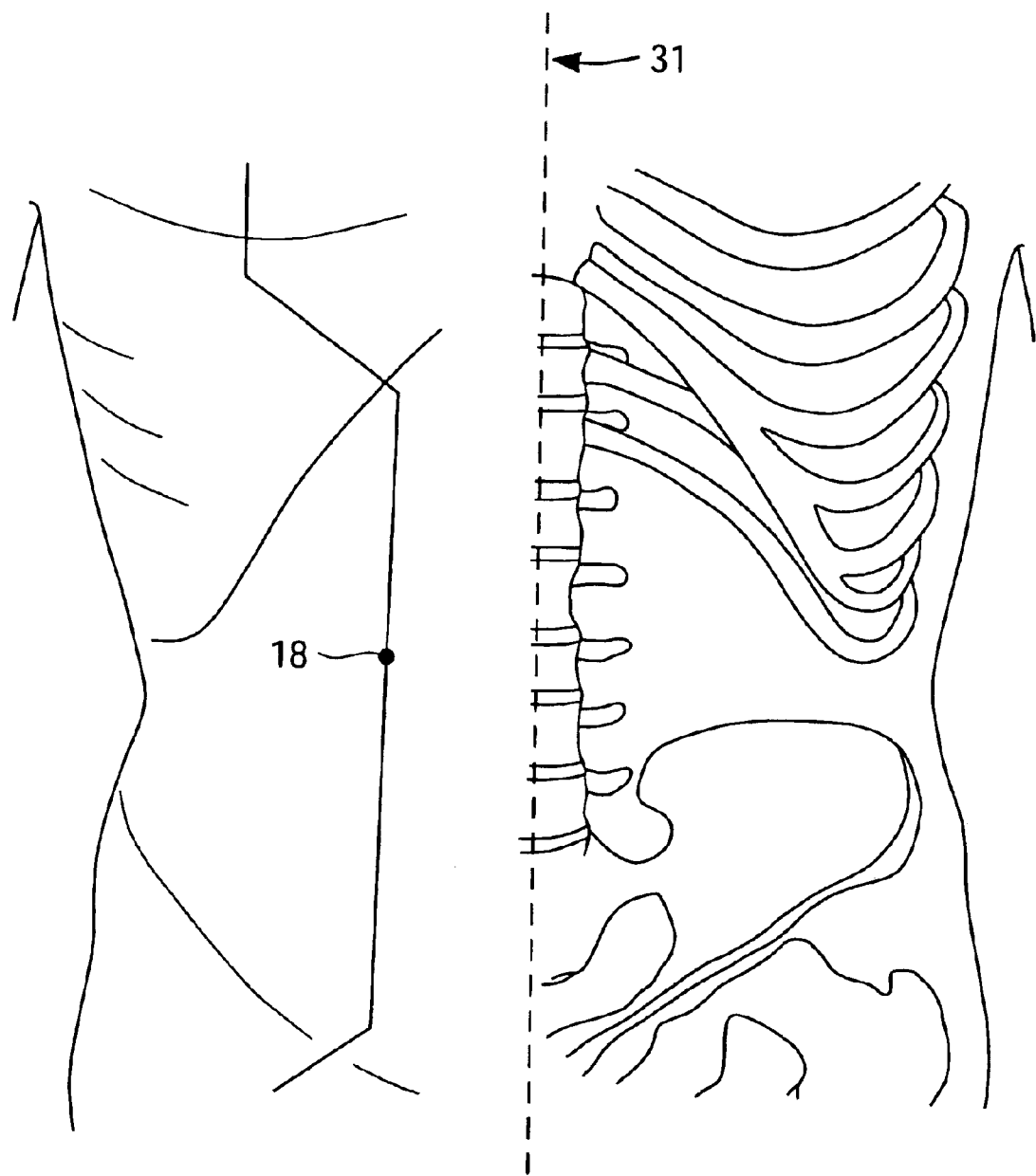
FIG. 4 is a front view of a human torso showing locations for needle and magnet placement in one embodiment of the invention.

The following method treats various ailments using a combination of acupuncture and magnets. In one embodiment, the treatment begins with the approximate placement of acupuncture needles on the ventral side of the wrist 30 (FIG. 1), the ventral (anterior) surface of the abdomen as divided by a medial line 31 (FIG. 4), and on the inside edge of the foot 32 (FIG. 3). A more precise location for the acupuncture needles involves placing the needles at pericardium 6 (PC6) 11, stomach 25 (ST25) 18, and spleen 4 (SP4) 12. Under other embodiments of the present invention, a more accurate placement of the acupuncture needles is disclosed by naming several acupuncture points 11–20.

Figure 2:
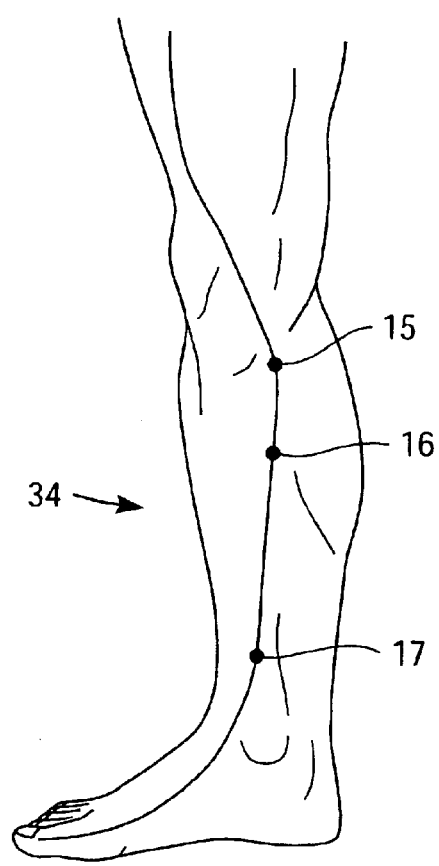
FIG. 2 is a view of a human right leg showing locations for needle and magnet placement in one embodiment of the invention.
Figure 5:
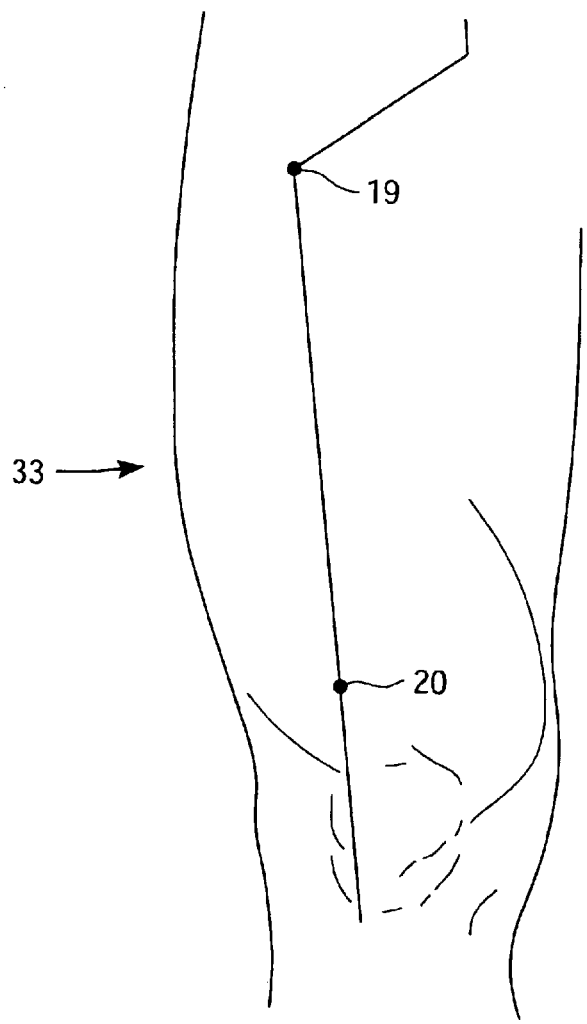
FIG. 5 is a front view of a ventral side of a right thigh showing locations for needle and magnet placement in one embodiment of the invention.

Depending on the circumstances, acupuncture needles can be placed at several additional locations on the body for treatment of various ailments. In another embodiment, there are two locations on the ventral (anterior) surface of the thigh 33 (FIG. 5), one at the top of the thigh and one above the knee. Two additional locations are located on the dorsal side of the foot (FIG. 2). One location is on the right half of the dorsal side of the foot and the other location is on the left half of the dorsal side of the foot. In addition to these general areas, acupuncture needles may also be placed more precisely at stomach 31 (ST31) 19, stomach 34 (ST34) 20, stomach 43 (ST43) 13, and gall bladder 41 (GB41) 14 (See FIGS. 5 and 3). Furthermore, in another embodiment, acupuncture needles may also be placed on the inside anterior surface of the leg 34 (FIG. 2), one near the knee, the mid-calf and proximal to the ankle. More particularly, acupuncture needles may be placed at spleen 9 (SP9) 15, spleen 8 (SP8)16, and spleen 6 (SP6) 17 (See FIG. 2).

The locations on the human body for placing the acupuncture needles and pins are shown generally in FIGS. 1–5. Even though FIGS. 1–5 only indicate locations on the right-hand side of the body, those skilled in the art realize that these acupuncture locations are also mirrored on the left-hand side of the body as well. Consequently, when the location of an acupuncture point is mentioned, it is generally understood that the named location can also include said location on either half of the human body.

Typically, the needles remain in place for about 30–40 minutes. However, the amount of time for the acupuncture treatment may vary. It is understood that acupuncture may vary the length of time for their acupuncture sessions and these normal variations are foreseeable and still covered under the present invention.

Figure 6A:
FIGS. 6A, 6B and 6C illustrate the various shapes of magnets that may be used in the embodiments of the present invention.
Figure 6B:
Figure 6C:
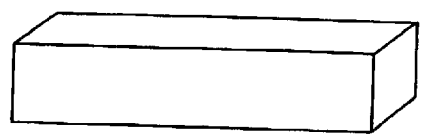

At the conclusion of the acupuncture treatment, the needles are removed and magnets are applied. FIG. 6 generally shows the different types of magnets that can be used. Circular disk magnets FIG. 6A, dome shaped magnets FIG. 5B rectangular bar magnets FIG. 5C have all been successfully used with this method. It is also understood that square, oval, circular or other shaped magnets would be acceptable; provided the magnets generally have a flat surface that ensures suitable contact of the magnet's surface with the patient's skin. Like the shape, the size of the magnet is not important and can vary depending on such things as wearer comfort, so long as the magnet covers the previous location of the acupuncture needles. When selecting magnets for use with this method, the strength of their magnetic flux is important. This method relies on the use of magnets with a magnetic flux greater than 800 gauss. More specifically, other embodiments of this invention successfully use magnets in the 1500–3000 gauss range.

The magnets are placed on the some locations that the acupuncture needles previously occupied 11–20. The magnets are placed on the skin and then secured with an attachment means. The invention does not depend on the method of attachment. Experiments using this method have successfully used adhesive tapes to secure the magnets in place. It is understood that the attachment means should not be limited to just tape. Various types of glues, Velcro, string, elastic bands, and the like could also be used to secure the magnets to the wearer. After being secured, the patient wears the magnets for a period of time.

In the various embodiments of the present invention, patients are urged to wear the magnets for about 8 hours. After a period of time, the magnets are removed and that concludes that acupuncture and magnet therapy session.

Another embodiment of the present invention concerns the treatment of obesity. Using the same procedure as previously disclosed, a similar treatment involving acupuncture and magnets could be used to help patients loose weight.

One example of a patient undergoing the acupuncture and magnet treatment was a male desiring to lose weight. The patient weighed 318 pounds and after undergoing nine acupuncture and magnet treatment sessions his weight dropped to 292 pounds.

Still another embodiment of the present invention is for the treatment of diabetes. The above-mentioned steps of acupuncture and magnets con be applied to patients for the management of their diabetes. An example of a patient using this method for controlling diabetes involved a woman seeking to regulate her diabetes. Before undergoing the acupuncture and magnet treatment, the patient's doctor administered a glycohemoglobin test. Found in red blood cells, glycohemoglobin is hemoglobin bound with glucose. Under normal circumstances, less than 7.0% of the hemoglobin the blood has glucose attached to it. In diabetics this number is often elevated. By monitoring a patient's glycohemoglobin, doctors are able to determine, on average, how well the patient's diabetes has been controlled during the previous 2–3 months.

The patient's initial test indicated her glycohemoglobin level was 12.8%. This was much higher than the normal levels, which are below 7%. After approximately two months of treatment, the patient's glycohemoglobin level was down to 5.9%, a decrease of 6.9%. The decreased glycohemoglobin levels indicated that for the few months prior to the section glycohemoglobin test the patent did well in regulating her diabetic condition.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments of the foregoing description, but rather is indicated by the appended claims. All changes that come within the meaning and range of equivalents within the claims are intended to be considered as being embraced within the spirit and scope of the claims.

What is claimed is:

1. A method for acupuncture and magnetic treatment on a human body, the method comprising:
    placing a plurality of acupuncture needles on a plurality of predetermined locations of the body, including:
        a. a ventral side near one or both wrists,
        b. one or more sides of a ventral surface of an abdomen as divided by a medial line, and
        c. an inside edge of one or more feet;
    removing said acupuncture needles;

placing one or more magnets on substantially the said predetermined locations.

2. The method according to claim 1, wherein acupuncture needles are placed approximately at a plurality of acupuncture points PC6, ST25, and SP4.

3. The method according to claim 1, further comprising:
placing acupuncture needles on a location approximate to a ventral side of an upper half of one or more thighs;
removing the acupuncture needles and placing one or more magnets substantially near said locations.

4. The method recited in claim 3, wherein acupuncture needles are placed at a position referenced by acupuncturists as ST31.

5. The method according to claim 1, further comprising:
placing acupuncture needles on a location approximate to a ventral side of one or more legs, just above a knee;
removing the acupuncture needles and placing one or more magnets on said locations.

6. The method recited in claim 5, wherein acupuncture needles are placed at a position referenced by acupuncturists as ST34.

7. The method according to claim 1, further comprising:
placing acupuncture needles on a location approximate to a dorsal side of one or more feet;
removing the acupuncture needles and placing one or more magnets on said locations.

8. The method recited in claim 7, wherein acupuncture needles are placed at a position referenced by acupuncturists as ST43.

9. The method according to claim 1, further comprising:
placing acupuncture needles on a location approximate to a dorsal side of one or more feet, proximal to an ankle;
removing the acupuncture needles and placing one or more magnets on said locations.

10. The method recited in claim 9, wherein acupuncture needles are placed at a position referenced by acupuncturists as GB41.

11. The method according to claim 1, further comprising:
placing acupuncture needles on a plurality of locations approximate to a dorsal side of one or more legs, between a knee and an ankle;
removing the acupuncture needles and placing one or more magnets on said locations.

12. The method according to claim 11, wherein acupuncture needles are placed at a plurality of locations referenced by acupuncturists as SP6, SP8 and SP9.

13. A method for weight loss involving acupuncture and magnetic treatment on a human body, the method comprising:
placing a plurality of acupuncture needles on a plurality of predetermined locations of the body, including:
a. a ventral side near one or both wrists,
b. one or more sides of a ventral surface of an abdomen as divided by a medial line, and
c. an inside edge of one or more feet;
removing said acupuncture needles;
placing one or more magnets on substantially the said predetermined locations.

14. The method according to claim 13, wherein acupuncture needles are placed approximately at a plurality of locations referenced by acupuncturists as PC6, ST25, and SP4.

15. The method according to claim 13, further comprising:
placing acupuncture needles on a location approximate to a ventral side of an upper half of one or more thighs;
removing the acupuncture needles and placing one or more magnets on said locations.

16. The method recited in claim 15, wherein acupuncture needles are placed at a position referenced by acupuncturists as ST31.

17. The method according to claim 13, further comprising:
placing acupuncture needles on a location approximate to a ventral side of one or more legs, just above a knee;
removing the acupuncture needles and placing one or more magnets on said locations.

18. The method recited in claim 17, wherein acupuncture needles are placed at a position referenced by acupuncturists as ST34.

19. The method according to claim 13, further comprising:
placing acupuncture needles on a location approximate to a dorsal side, of one or more feet;
removing the acupuncture needles and placing one or more magnets on said locations.

20. The method recited in claim 19, wherein acupuncture needles are placed at a position referenced by acupuncturists as ST43.

21. The method according to claim 13, further comprising:
placing acupuncture needles on a location approximate to a dorsal side of one or more feet, proximal to an ankle;
removing the acupuncture needles and placing one or more magnets on said locations.

22. The method recited in claim 21, wherein acupuncture needles are placed at a position referenced by acupuncturists as GB41.

23. A method for acupuncture and magnetic treatment on a human body, particularly for weight loss or treating diabetes, the method comprising:
placing a plurality of acupuncture needles on a plurality of predetermined locations of the body, including:
a. a ventral side of one or both wrists,
b. one or more sides of a ventral surface of an abdomen as divided by a medial line, and
c. an inside edge of one or more feet;
removing said acupuncture needles;
placing one or more magnets on substantially the said predetermined locations.

24. The method according to claim 23, wherein acupuncture needles are placed approximately at a plurality of acupuncture points PC6, ST25, and SP4.

25. The method according to claim 23, further comprising:
placing acupuncture needles on a location approximate to a ventral side of an upper half of one or more thighs;
removing the acupuncture needles and placing one or more magnets on said locations.

26. The method according to claim 25, wherein acupuncture needles are placed at a position referenced by acupuncturists as ST31.

27. The method according to claim 23, further comprising:
placing acupuncture needles on a location approximate to a ventral side of one or more legs, just above a knee;
removing the acupuncture needles and placing one or more magnets on said locations.

28. The method according to claim 27, wherein acupuncture needles are placed at a position referenced by acupuncturists as ST34.

29. The method according to claim 23, further comprising:
   placing acupuncture needles on a location approximate to a dorsal side of one or more feet;
   removing the acupuncture needles and placing one or more magnets on said locations.

30. The method recited in claim 29, wherein acupuncture needles are placed at a position referenced by acupuncturists as ST43.

31. The method according to claim 23, further comprising:
   placing acupuncture needles on a location approximate to a dorsal side of one or more feet, proximal to an ankle;
   removing the acupuncture needles and placing one or more magnets on said locations.

32. The method recited in claim 31, wherein acupuncture needles are placed at a position referenced by acupuncturists as GB41.

33. A method for acupuncture and magnetic treatment on a human body, particularly for weight loss or treating diabetes, the method comprising:
   placing a plurality of acupuncture needles on a plurality of predetermined locations of the body, including:
      a. PC6,
      b. ST25, and
      c. SP4;
   removing said acupuncture needles after a set time;
   using an attachment means to place one or more magnets on substantially the said predetermined locations for a period of time.

34. The method according to claim 33, wherein a set time is approximately about 30 to about 40 minutes.

35. The method according to claim 33, wherein a period of time is about 8 hours.

36. The method according to claim 33, further comprising:
   placing acupuncture needles on a location approximate to a ventral side of an upper half of one or more thighs;
   removing the acupuncture needles and placing one or more magnets on said locations.

37. The method recited in claim 36, wherein acupuncture needles are placed at a position referenced by acupuncturists as ST31.

38. The method according to claim 33, further comprising:
   placing acupuncture needles on a location approximate to a ventral side of one or more legs, just above a knee;
   removing the acupuncture needles and placing one or more magnets on said locations.

39. The method recited in claim 38, wherein acupuncture needles are placed at a position referenced by acupuncturists as ST34.

40. The method according to claim 33, further comprising:
   placing acupuncture needles on a location approximate to a dorsal side of one or more feet;
   removing the acupuncture needles and placing one or more magnets on said locations.

41. The method recited in claim 40, wherein acupuncture needles are placed at a position referenced by acupuncturists as ST43.

42. The method according to claim 33, further comprising:
   placing acupuncture needles on a location approximate to a dorsal side of one or more feet, proximal to an ankle;
   removing the acupuncture needles and placing one or more magnets on said locations.

43. The method recited in claim 42, wherein acupuncture needles are placed at a position referenced by acupuncturists as GB41.

44. The method according to claim 33, in which a side of a magnet coming into contact with the skin surface of a human body is essentially flat.

45. The method according to claim 33, further comprising: magnets having a diameter of approximately 8–13 mm.

46. The method according to claim 33, further comprising: magnets with a magnetic flux density of more than 800 Gauss.

47. The method according to claim 46, further comprising: magnets with a magnetic flux density of about 1500–3000 Gauss.

* * * * *